US005618762A

United States Patent [19]
Shirakawa et al.

[11] Patent Number: 5,618,762
[45] Date of Patent: Apr. 8, 1997

[54] LIGHT-WEIGHT ANTIBACTERIAL CERAMIC AND ANTIBACTERIAL CERAMIC FILTER

[75] Inventors: Hiroshi Shirakawa, Kagamigahara; Osamu Yamakawa, Kani; Hiroaki Nihonmatsu, Gifu; Kiminori Atsumi, Saitama, all of Japan

[73] Assignees: NGK Insulators, Ltd.; NGK Adrec Co. Ltd., both of Nagoya; Sangi Co. Ltd., Tokyo, all of Japan

[21] Appl. No.: 439,374

[22] Filed: May 11, 1995

[30] Foreign Application Priority Data

May 16, 1994 [JP] Japan .................................. 6-101429

[51] Int. Cl.$^6$ .............................. C04B 35/00; A01N 59/16; B01D 39/20
[52] U.S. Cl. .................... 501/1; 106/15.05; 106/18.31; 106/18.36; 210/500.25; 210/510.1; 424/618; 424/620; 424/630; 424/641; 424/649; 424/650; 424/652; 424/654; 424/655; 501/80; 501/81; 501/82; 501/83; 501/102; 501/123; 501/127; 501/133
[58] Field of Search ................... 501/1, 102, 123, 501/127, 133, 153, 154, 80, 81, 82, 83; 106/15.05, 18.36, 18.31; 210/500.25, 510.1; 424/618, 620, 630, 641, 649, 650, 652, 654, 655

[56] References Cited

U.S. PATENT DOCUMENTS

| 4,145,291 | 3/1979 | Console et al. ................. 210/232 |
|---|---|---|
| 5,009,898 | 4/1991 | Sakuma et al. ................. 106/35 |
| 5,011,602 | 4/1991 | Totani et al. ................. 210/484 |
| 5,064,599 | 11/1991 | Ando et al. ................. 264/237 |
| 5,151,122 | 9/1992 | Atsumi et al. ................. 106/18.36 |
| 5,187,124 | 2/1993 | Kweon ................. 501/1 |
| 5,266,534 | 11/1993 | Atsumi et al. ................. 106/18.36 |
| 5,348,577 | 9/1994 | Atsumi et al. ................. 106/18.31 |

FOREIGN PATENT DOCUMENTS

| 0360593A2 | 3/1990 | European Pat. Off. . |
|---|---|---|
| 0427704A1 | 5/1991 | European Pat. Off. . |
| 2-180742 | 7/1990 | Japan . |
| 2-172467 | 7/1990 | Japan . |
| 2-213350 | 8/1990 | Japan . |
| 5-000154 | 1/1993 | Japan . |
| 5-124919 | 5/1993 | Japan . |
| 6-001708 | 1/1994 | Japan . |
| 1169312 | 11/1969 | United Kingdom ................. 501/1 |
| 2238044 | 5/1991 | United Kingdom . |

*Primary Examiner*—Anthony Green
*Attorney, Agent, or Firm*—Ronald J. Kubovcik, Esq.

[57] ABSTRACT

An antibacterial ceramic contains an antibacterial material produced by loading an antibacterial metal such as silver on a calcium ceramic carrier and an inorganic material such as cordierite, and has a bulk density of 0.6–1.2 g/cm$^3$. An antibacterial ceramic filter contains an antibacterial material produced by loading an antibacterial metal such as silver on a calcium ceramic carrier, an aggregate such as mullite, and a binder such as frit, and has a porosity of 20% or more. The light-weight antibacterial ceramic is suitably applicable to a roof garden or the like. The antibacterial ceramic filter can remove and extirpate various bacteria and suspensions.

12 Claims, No Drawings

LIGHT-WEIGHT ANTIBACTERIAL CERAMIC AND ANTIBACTERIAL CERAMIC FILTER

BACKGROUND OF THE INVENTION AND RELATED ART STATEMENT

The present invention relates to an antibacterial ceramic and an antibacterial ceramic filter. More particularly, the present invention relates to a lightweight antibacterial ceramic, a method for producing the lightweight antibacterial ceramic, and an antibacterial ceramic filter which can remove and extirpate various bacteria.

There has conventionally been known antibacterial ceramics having an antibacterial metal such as silver, copper, and zinc loaded on a ceramic. Such antibacterial ceramics are used as soil conditioners and water conditioners because of their antibacterial property, anti-mildew property, and water-holding property. An antibacterial ceramic having the shape of a ball has been used for cultivation of chicks, prawns, or the like. An antibacterial ceramic having the shape of a pellet with enlarged specific surface area or the shape of a Rasching ring has been used for treating water to improve its quality.

Incidentally, the aforementioned antibacterial ceramic is formed to be relatively porous so as to enhance its antibacterial property. However, many of such conventional antibacterial ceramics have been dense and heavy. There has also been known antibacterial materials made by adding an antibacterial metal to a plastic or a glass. However, such antibacterial materials have a low antibacterial property because of low porosity.

There also has been known a ceramic filter used as a precise filtering film. This filter can remove mildew and various bacteria in a liquid.

In the construction of a garden, either in or on the roof of a building, both the soil and the soil conditioners used in the garden must be lightweight to avoid exceeding the structural strength of the building. However, there has been a problem that the aforementioned antibacterial ceramics are not suitable for a roof garden or the like since they are relatively heavy. On the other hand, there has been another problem that roots of plants in roof gardens are liable to rot because roof gardens suffer from poor drainage, and as a result, such plants have short lives.

There has been still another problem that conventional ceramic filters are not always effective to completely remove various bacteria from a liquid because of the diameters of the pores in such filters.

SUMMARY OF THE INVENTION

The present invention has been achieved in consideration of such conventional problems. An object of the present invention is to provide a lightweight antibacterial ceramic which is suitably applicable to, for example, a roof garden, and a method for producing the lightweight antibacterial ceramic.

Another object of the invention is to provide an antibacterial ceramic filter which has an antibacterial property which can remove and extirpate various bacteria and floats.

As a result of energetic studies to achieve the aforementioned objects, the present inventors found that the objects can be achieved by firing a mixture of an antibacterial metal and a specific material and controlling the bulk density and the porosity of the sintered body, which led to the completion of the present invention.

Therefore, the lightweight antibacterial ceramic of the present invention includes: an antibacterial material of 0.01–20 wt % in which an antibacterial metal or metallic ion is loaded on a carrier; and an oxide inorganic material and/or a non-oxide inorganic material of 99.9–80 wt %; wherein the antibacterial ceramic has a particle bulk density of 0.6–2.0 g/cm$^3$.

The method for producing the lightweight antibacterial ceramic of the present invention includes the steps of: preparing an antibacterial ceramic material by loading an antibacterial metal or metallic ion on a carrier; mixing the obtained antibacterial ceramic material of 0.01–20 wt % with an oxide inorganic material and/or a non-oxide inorganic material of 99.9–80 wt % to obtain a first mixture; mixing a combustible of 5–50 weight parts with the mixture of 100 weight parts to obtain a second mixture; and firing the second mixture at a temperature of 500°–1300° C.

The antibacterial ceramic filter of the present invention includes: an aggregate phase comprising an oxide inorganic material and/or a non-oxide inorganic material; and an inorganic binder phase; wherein the antibacterial ceramic filter has: a base material phase of 99.9–80 wt % including the aggregate and the inorganic binder phase; and an antibacterial material of 0.01–20 wt % comprising a carrier and an antibacterial metal or metallic ion loaded on the carrier; and the antibacterial ceramic filter has a porosity of 20% or more.

In the antibacterial ceramic of the present invention, the ceramic can be lightened and the surface area can be enlarged because the bulk density of the ceramic particles is appropriately controlled. Therefore, the antibacterial ceramic can be suitably used for applications such as a roof garden and the probability that the ceramic will come in contact with bacteria is increased, which improves its antibacterial property.

On the other hand, the antibacterial ceramic filter of the present invention can not only remove but also extirpate bacteria and further improve the clearness of a liquid. It is also possible to make the diameter of pores a little larger than in conventional filters so that the filtering time is shortened without decreasing the clearness of the liquid because the antibacterial ceramic of the present invention can extirpate the bacteria which passes through the pores and can not be removed.

DETAILED DESCRIPTION OF THE INVENTION

The antibacterial ceramic of the present invention is hereinbelow described in more detail.

The antibacterial ceramic of the present invention contains an antibacterial material made by loading an antibacterial metal or metallic ion on a carrier. The antibacterial material preferably has a composition of an antibacterial metal or metallic ion of 0.01–20 wt % and a carrier of 99.9–80 wt %.

When the aforementioned antibacterial metal or metallic ion is present in an amount less than 0.01 wt %, the antibacterial ceramic has a low antibacterial property. When the antibacterial metal or metallic ion is present in an amount more than 20 wt %, the cost of the antibacterial ceramic becomes high because the cost of such a metal or metallic ion is high.

The antibacterial metal or metallic ion may be silver, copper, zinc, platinum, tin, arsenic, lead, cadmium, chromium, or any mixture of these components.

The aforementioned carrier may be phosphate, silica, zeolite, or any mixture of these components. Phosphate for the carrier may be calcium phosphate, zinc phosphate, zirconium phosphate, aluminum phosphate, or any mixture of these components. Calcium phosphate for the carrier may be tricalcium phosphate, calcium hydrogenphosphate, calcium pyrophosphate, calcium metaphosphate, hydroxy apatite, apatite halide, or any mixture of these components.

The methods for loading the antibacterial metal or metallic ion on the aforementioned carrier are not limited. Suitable methods include, for example, ion exchange, a firing treatment at 800° C. or higher after ion exchange, or firing at about 80° C. or higher an aqueous solution containing a water-soluble salt having an antibacterial component and then collecting the precipitate. Among these methods, the preferred method is the one in which a water-soluble salt having an antibacterial component is used because this method prevents elusion of the antibacterial metallic component and reduces the production cost.

Incidentally, each of the aforementioned calcium ceramics to be used for the carrier is highly safe for a human body. Further, such calcium ceramics readily absorb a water-soluble salt of an antibacterial metal and metallic ion when an antibacterial metal is loaded. Therefore, the calcium ceramics are suitably applicable to the present invention.

The antibacterial ceramic of the present invention includes 1) the aforementioned antibacterial material of 0.01–20 wt % and 2) an oxide inorganic material and/or a non-oxide inorganic material of 99.9–80 wt %.

It is not preferred that the antibacterial material be less than 0.01 wt % or more than 20 wt % because the antibacterial property decreases or the production cost is high, respectively.

The aforementioned oxide inorganic material or non-oxide inorganic material may be any material which is water-insoluble and harmless to human bodies, animals and plants. The oxide inorganic material may be alumina, cordierite, mullite, silica, clay, or the like. The non-oxide inorganic material may be silicon carbide, silicon nitride, or aluminum nitride. Note that a self-sintering material such as clay or an inorganic binder such as a frit can be mixed with these inorganic materials.

Further, the antibacterial ceramic of the present invention is light because it has a particle bulk density of 0.6–2.0 g/cm$^3$, preferably 0.6–1.2 g/cm$^3$. Therefore, the antibacterial ceramic of the present invention can be used as a soil conditioner, particularly for a garden on the roof, or the like, and its conveyability is excellent. It is not preferred that the antibacterial ceramic has a bulk density of less than 0.6 g/cm$^3$ because it is then so light that it can be scattered in the wind. It is not preferred either that the antibacterial ceramic has a bulk density of more than 2.0 g/cm$^3$ because it is then too heavy and the antibacterial property decreases because the porosity of the ceramic is low.

Since the aforementioned antibacterial ceramic of the present invention has an excellent antibacterial property and is safe for human bodies, the ceramic can be used not only as a soil conditioner for a garden on the roof or the like but also applied to soil for home gardening. Further, the ceramic can be used as sand for evacuation by a pet such as a dog or a cat. The antibacterial ceramic of the present invention can prevent various bacteria from generating and make animals' and plants' lives longer while satisfying the proof load on a building.

The method for producing an antibacterial ceramic of the present invention is hereinbelow explained.

The antibacterial ceramic of the present invention is produced by a method including the steps of: preparing an antibacterial ceramic material by loading an antibacterial metal or metallic ion on a carrier; mixing the obtained antibacterial ceramic material of 0.01–20 wt % with an oxide inorganic material and/or a non-oxide inorganic material of 99.9–80 wt % to obtain a first mixture; mixing a combustible of 5–50 weight parts with the mixture of 100 weight parts to obtain a second mixture; and firing the second mixture at a temperature of 500°–1300° C.

The aforementioned combustible may be a carbon powder, a grain powder such as wheat flour or rice flour, a sawdust, or the like. These combustibles are consumed by the aforementioned firing and have the function of making the resultant antibacterial ceramic light and porous. It is not preferred that the combustible be added in an amount of less than 5 weight parts or more than 50 weight parts because the effect of lowering the bulk specific gravity is small or the resultant ceramic is liable to be crushed, respectively. Note that the order in which the antibacterial material, the inorganic material, and the combustible are added is not limited, and any order is acceptable if the aforementioned powder for firing having a predetermined composition can be obtained.

The antibacterial ceramic filter of the present invention is now described in detail.

The antibacterial ceramic filter of the present invention includes: the aforementioned antibacterial material of 0.01–20 wt %; and a base material phase of 99.9–80 wt % having 1) an aggregate phase containing an oxide inorganic material and/or a non-oxide inorganic material and 2) an inorganic binder phase.

The oxide inorganic material and the non-oxide inorganic material to be used for forming an aggregate phase by firing are not limited, and any water-insoluble material which is harmless to human bodies, animals, and plants can be employed. The oxide inorganic material may be alumina, mullite, zirconia, andalusite, silica ceramic material, glass, or the like. The non-oxide inorganic material may be silicon carbide, silicon nitride, and aluminum nitride.

The aforementioned inorganic binder may be an inert self-sintering material such as clay or inorganic binding material such as a frit. The ratio of the inorganic binder to the aforementioned aggregate is preferably within the range of 1–50 wt %. When the ratio is less than 1 wt %, the resultant filter does not have sufficient strength. When the ratio is more than 50 wt %, the resultant filter has a low porosity, which lowers water permeability.

Each of the pores of the ceramic filter of the present invention preferably has a diameter ranging 20 to 8000 μm. When the diameter of a pore is less than 20 μm, the pore is prone to be clogged up with impurities, which lowers water-permeability of the filter in the early stages. When the diameter of a pore is more than 800 μm, the filter has a low antibacterial property.

Incidentally, the configuration of the antibacterial ceramic filter of the present invention is not particularly limited, and various kinds of configurations such as the shape of a plate, a cylinder, or the like can be employed. The use of the ceramic filter is not limited, and it can be suitably used for purifying water in a Japanese traditional bath tub and water for a large bathing place such as a swimming pool.

When the antibacterial ceramic filter of the present invention is in use, a particular tank or the like is not necessary, and the flow passage or the like is directly equipped with the ceramic filter.

The method for producing the antibacterial ceramic filter of the present invention is hereinafter described.

The method for producing the ceramic filter of the present invention includes the steps of: mixing the aforementioned antibacterial material of 0.01–20 wt % with the aforementioned mixture of 99.9–80 wt % containing an aggregate and an inorganic binder phase; adding a combustible of 0–30 weight parts to the obtained mixture of 100 weight parts to prepare another mixture for forming a compact; preparing a compact having a predetermined shape by the mixture for forming a compact; and firing the compact at 1300° C. or less, preferably at 700°–1000° C.

Incidentally, the order of adding the antibacterial material, the aggregate, the inorganic binder, and the combustible is not limited in the aforementioned method, and any order is acceptable if the aforementioned mixture having a predetermined composition for forming a compact can be obtained.

In this method, the 50% average particle diameter of the aggregate is preferably 0.1–20 mm. When the diameter is less than 0.1 mm, water-permeability becomes low because of clogging in the early stages though the discriminating ability of the filter is high. When the diameter is more than 20 mm, the filter has a low antibacterial property, and the discriminating ability of the filter is lowered.

The aforementioned inorganic binding material has a particle diameter of 100 µm or less, preferably 44 µm or less, and the blending ratio of the inorganic binding material to the aforementioned aggregate is preferably about 1–50%.

Further, the porosity and the pore diameter of the ceramic filter can be adjusted as necessary by adding the aforementioned combustible. For example, the combustible may have a particle diameter of 1–100 µm.

The present invention is hereinbelow described in more detail with reference to the following Examples. However, the present invention is not limited to these Examples.

EXAMPLES 1–6

There were kneaded by a kneader a mixture of an oxide inorganic material (base material A) mainly consisting of cordierite, an antibacterial material produced by loading Ag on hydroxy apatite, an appropriate amount of a binder, and a combustible of 10–50 weight parts to the base material A of 100 weight parts in the ratio shown in Table 1. The obtained mixture was dried at 110° C. and then fired at 1100° C. in ambient air. Then, it was crushed by a roll crusher so as to obtain a lightweight antibacterial ceramic. Incidentally, in Tables 1–9, "amount of metal" refers to the total amount of Ag or the like contained in each lightweight antibacterial ceramic.

The obtained lightweight antibacterial ceramic was dried and then measured for dry weight. The dried ceramic was treated for three hours under a reduced pressure of 730 mmHg and then measured for weight in water. Then the ceramic saturated with water was measured for weight. The particle bulk density of the ceramic was calculated from the obtained three kinds of weights. The results are shown in Table 1.

Performance evaluation (1) Brittleness

Impact was given on each of the lightweight antibacterial ceramics to be crushed by an apparatus for Charpy impact test on conditions that a pendulum has a weight of 1 kg, a pendulum rod has a length of 50 cm, and an angle of oscillation between the perpendicular portion and the top portion of the swing of 45° C. The crushed lightweight antibacterial ceramic was sieved by a sieve #100, and the ceramic was measured for brittleness by calculating the ratio of amount of the crushed ceramic which passed the sieve. The results are shown in Table 1. In Table 1, the marks ⊙, ○, Δ, and X denote as follows:

⊙ ... 10% or less was passed through the sive.
○ ... 10–20% was passed.
Δ ... 20–50% was passed.
× ... 50% or more was passed.

(2) Antibacterial property

Two liquids each containing about $10^6$ colon bacilli were prepared for each lightweight ceramic. To one liquid was added a lightweight antibacterial ceramic of 1.5 wt %, and to the other liquid was added the same lightweight antibacterial ceramic of 10 wt %. After 6 hours and after 24 hours, the two liquids for each kind of ceramic were measured for the number of colon bacilli. The antibacterial property of each lightweight antibacterial ceramic was judged from the ratio of decreased colon bacilli. The results are shown in Table 1.

COMPARATIVE EXAMPLES 1–3

The ceramics were prepared and tested in the same manner as in Examples 1–6 except that the bulk density was varied. The results are shown in Table 1.

EXAMPLES 7–14

There were used a mixture (base material B) of cordierite and frit as an oxide inorganic material and a hydroxy apatite on which Ag and Zn were loaded as an antibacterial material. Except for based material B, the ceramics were prepared and tested in the same manner as in Examples 1–5. The results are shown in Table 2.

COMPARATIVE EXAMPLE 4

The ceramic was prepared and tested in the same manner as in Examples 6–13 except that an antibacterial material was not added. The results are shown in Table 2.

COMPARATIVE EXAMPLE 15–17

The ceramics were prepared and tested in the same manner as in Examples 1–except that mullite (base material C) was used as an oxide inorganic material and calcium hydrogenphosphate on which Cu was loaded was used as an antibacterial material. The results are shown in Table 3.

EXAMPLES 18–20

The ceramics were prepared and tested in the same manner as in Examples 15–17 except that silicon nitride (base material D) was used as a non-oxide inorganic material.

EXAMPLES 21–26

The ceramics were prepared and tested in the same manner as in Examples 1–6 except that a mixture of cordierite and clay was used as an oxide inorganic material, that calcium phosphate on which Ag was loaded was used as an antibacterial material, and that each of the ceramics was fired at the temperature shown in Table 4.

EXAMPLES 27–34

There were mixed 1) a base material F containing mullite (aggregate) having a 50% particle diameter of 1.0 mm and a frit (inorganic binder), 2) an antibacterial material produced by loading copper on calcium hydrogenphosphate, and 3) an appropriate amount of binder in a KANTO mixer so as to have the ratio shown in Table 5. The obtained mixture was subjected to a hydraulic press under a pressure of 300 kg/cm$^2$ given by a pressurizing substance having dimensions of 300×300×30 mm (thickness) so as to obtain a compact having the shape of a plate. The compact was dried at 110° C. and then fired at 900° C. in ambient air so as to obtain an antibacterial ceramic filter.

Each of the obtained antibacterial ceramic filters was measured for porosity in the same manner as the aforementioned measurement for particle bulk density. The results are shown in Table 5. The antibacterial property of each of the antibacterial ceramic filters was measured in the same manner, and the results are shown in Table 5.

COMPARATIVE EXAMPLE 5

The ceramic filter was obtained and tested in the same manner as in Examples 27–34 except that an antibacterial material was not added. The results are shown in Table 5.

EXAMPLES 35–38, COMPARATIVE EXAMPLE 6

The ceramic filters were obtained and tested in the same manner as in Examples 27–34 except that there were used 1) a base material G containing alumina having a 50% average particle diameter of 0.5 mm and a frit and 2) an antibacterial material produced by loading Ag and Zn on hydroxy apatite so as to vary the porosity of each filter. The results are shown in Table 6.

EXAMPLES 39–46

The ceramic filters were obtained and tested in the same manner as in Examples 27–34 except that the 50% average particle diameter of the aggregate in base material F were varied. The results are shown in Table 7.

EXAMPLES 47–54

The ceramic filters were obtained and tested in the same manner as in Examples 39–46 except that an antibacterial material of 10 wt % is added. The results are shown in Table 8.

EXAMPLES 55–57

The ceramic filters were obtained and tested in the same manner as in Examples 27–34 except that the 50% average particle diameter of the aggregate and the porosity were varied. The results are shown in Table 9.

EXAMPLES 58–60

The ceramic filters were obtained and tested in the same manner as in Examples 55–57 except that a mixture of non-oxide SiC (aggregate) and a frit was used. The results are shown in Table 9.

TABLE 1

| | Base Material A (wt %) | Antibacterial Material (wt %) | Amount of Metal (wt %) | Bulk Density (g/cm$^3$) | *1 Brittleness | *2 Antibacterial Property | Amount of Combustible (weight parts) |
| --- | --- | --- | --- | --- | --- | --- | --- |
| Example | | | | | | | |
| 1 | 90 | 10 | 1 | 0.6 | ○ | ◉ | 50 |
| 2 | " | " | " | 0.8 | ◉ | ◉ | 40 |
| 3 | " | " | " | 0.9 | ◉ | ◉ | 30 |
| 4 | " | " | " | 1.0 | ◉ | ◉ | 25 |
| 5 | " | " | " | 1.2 | ◉ | ○ | 15 |
| 6 | " | " | " | 1.8 | ◉ | ○ | 10 |
| Comp. Example | | | | | | | |
| 1 | 90 | 10 | 1 | 0.1 | X | ◉ | 90 |
| 2 | " | " | " | 0.3 | Δ | ◉ | 60 |
| 3 | " | " | " | 2.5 | ◉ | X | 0 |

*1 ... ◉; Very hard to crush ○; Hard to crush Δ; Easy to crush X; Very easy to crush
*2 ... ◉; Highly effective ○; Effective Δ; A little effective X; Not effective

TABLE 2

| | Base Material B (wt %) | Antibacterial Material (wt %) | Amount of Metal (wt %) | Bulk Density (g/cm$^3$) | *1 Brittleness | *2 Antibacterial Property |
| --- | --- | --- | --- | --- | --- | --- |
| Example | | | | | | |
| 7 | 99.99 | 0.01 | 0.0001 | 1.0 | ◉ | Δ |
| 8 | 99.9 | 0.1 | 0.001 | 1.0 | ◉ | Δ |
| 9 | 99 | 1 | 0.01 | 1.0 | ◉ | ○ |
| 10 | 97 | 3 | 0.03 | 1.0 | ◉ | ◉ |
| 11 | 95 | 5 | 0.05 | 1.0 | ◉ | ◉ |

TABLE 2-continued

|  | Base Material B (wt %) | Antibacterial Material (wt %) | Amount of Metal (wt %) | Bulk Density (g/cm³) | *1 Brittleness | *2 Antibacterial Property |
|---|---|---|---|---|---|---|
| 12 | 90 | 10 | 0.1 | 1.0 | ⊚ | ⊚ |
| 13 | 80 | 20 | 0.2 | 1.0 | ⊚ | ⊚ |
| 14 | 50 | 50 | 0.5 | 1.0 | ⊚ | ⊚ |
| Comp. Exam. |  |  |  |  |  |  |
| 4 | 100 | 0 | 0 | 1.0 | ⊚ | X |

*1 ... ⊚; Very hard to crush O; Hard to crush Δ; Easy to crush X; Very easy to crush
*2 ... ⊚; Highly effective O; Effective Δ; A little effective X; Not effective

TABLE 3

| Example |  | Antibacterial Material (wt %) | Amount of Metal (wt %) | Bulk Density (g/cm³) | *1 Brittleness | *2 Antibacterial Property |
|---|---|---|---|---|---|---|
|  | Base Material C (wt %) |  |  |  |  |  |
| 15 | 99 | 1 | 0.1 | 0.9 | ⊚ | O |
| 16 | 94 | 6 | 0.5 | 0.6 | O | ⊚ |
| 17 | 90 | 10 | 1 | 1.0 | ⊚ | ⊚ |
|  | Base Material D (wt %) |  |  |  |  |  |
| 18 | 99 | 1 | 0.1 | 0.9 | ⊚ | O |
| 19 | 95 | 5 | 0.5 | 0.6 | O | ⊚ |
| 20 | 90 | 10 | 1 | 1.0 | ⊚ | ⊚ |

*1 ... ⊚; Very hard to crush O; Hard to crush Δ; Easy to crush X; Very easy to crush
*2 ... ⊚; Highly effective O; Effective Δ; A little effective X; Not effective

TABLE 4

|  | Base Material E (wt %) | Antibacterial Material (wt %) | Amount of Metal (wt %) | Firing Temperature (°C.) | Bulk Density (g/cm³) | *1 Brittleness | *2 Antibacterial Property |
|---|---|---|---|---|---|---|---|
| Example |  |  |  |  |  |  |  |
| 21 | 97 | 3 | 0.6 | 1000 | 1.0 | Δ | ⊚ |
| 22 | 97 | 3 | 0.6 | 1100 | 1.0 | O | ⊚ |
| 23 | 97 | 3 | 0.6 | 1200 | 1.0 | ⊚ | O |
| 24 | 97 | 3 | 0.6 | 1300 | 1.0 | ⊚ | O |
| 25 | 97 | 3 | 0.6 | 1400 | 1.0 | ⊚ | Δ |
| 26 | 97 | 3 | 0.6 | 800 | 1.0 | Δ | ⊚ |

*1 ... ⊚; Very hard to crush O; Hard to crush Δ; Easy to crush X; Very easy to crush
*2 ... ⊚; Highly effective O; Effective Δ; A little effective X; Not effective

TABLE 5

|  | Base Material F (wt %) | Antibacterial Material (wt %) | Amount of Metal (wt %) | Particle Diameter of Aggregate (m) | Porosity (%) | *1 Antibacterial Property |
|---|---|---|---|---|---|---|
| Example |  |  |  |  |  |  |
| 27 | 99.99 | 0.01 | 0.001 | 1.0 | 40 | Δ |
| 28 | 99.9 | 0.1 | 0.01 | 1.0 | 40 | O |

TABLE 5-continued

|   | Base Material F (wt %) | Antibacterial Material (wt %) | Amount of Metal (wt %) | Particle Diameter of Aggregate (m) | Porosity (%) | *1 Antibacterial Property |
|---|---|---|---|---|---|---|
| 29 | 99 | 1 | 0.1 | 1.0 | 40 | ○ |
| 30 | 97 | 3 | 0.3 | 1.0 | 40 | ⊙ |
| 31 | 95 | 5 | 0.5 | 1.0 | 40 | ⊙ |
| 32 | 90 | 10 | 1 | 1.0 | 40 | ⊙ |
| 33 | 80 | 20 | 2 | 1.0 | 40 | ⊙ |
| 34 | 40 | 60 | 5 | 1.0 | 40 | ⊙ |
| Comp. Exam. | | | | | | |
| 5 | 100 | 0 | 0 | 1.0 | 40 | X |

*1 ... ⊙; Highly effective ○; Effective Δ; A little effective X; Not effective

TABLE 6

|   | Base Material G (wt %) | Antibacterial Material (wt %) | Amount of Metal (wt %) | Particle Diameter of Aggregate (m) | Porosity (%) | *1 Antibacterial Property |
|---|---|---|---|---|---|---|
| Example | | | | | | |
| 35 | 90 | 10 | 0.1 | 0.5 | 20 | Δ |
| 36 | 90 | 10 | 0.1 | 0.5 | 30 | ○ |
| 37 | 90 | 10 | 0.1 | 0.5 | 40 | ⊙ |
| 38 | 90 | 10 | 0.1 | 0.5 | 60 | ⊙ |
| Comp. Exam. | | | | | | |
| 6 | 90 | 10 | 0.1 | 0.5 | 10 | X |

*1 ... ⊙; Highly effective ○; Effective Δ; A little effective X; Not effective

TABLE 7

|   | Base Material F (wt %) | Antibacterial Material (wt %) | Amount of Metal (wt %) | Particle Diameter of Aggregate (m) | Porosity (%) | *1 Antibacterial Property |
|---|---|---|---|---|---|---|
| Example | | | | | | |
| 39 | 99 | 1.0 | 0.005 | 0.05 | 40 | ⊙ |
| 40 | 99 | 1.0 | 0.005 | 0.1 | 40 | ⊙ |
| 41 | 99 | 1.0 | 0.005 | 0.5 | 40 | ⊙ |
| 42 | 99 | 1.0 | 0.005 | 1.0 | 40 | ⊙ |
| 43 | 99 | 1.0 | 0.005 | 5 | 40 | ○ |
| 44 | 99 | 1.0 | 0.005 | 10 | 40 | ○ |
| 45 | 99 | 1.0 | 0.005 | 20 | 40 | Δ |
| 46 | 99 | 1.0 | 0.005 | 40 | 40 | Δ |

*1 ... ⊙; Highly effective ○; Effective Δ; A little effective X; Not effective

TABLE 8

|   | Base Material F (wt %) | Antibacterial Material (wt %) | Amount of Metal (wt %) | Particle Diameter of Aggregate (m) | Porosity (%) | *1 Antibacterial Property |
|---|---|---|---|---|---|---|
| Example | | | | | | |
| 47 | 90 | 10 | 0.05 | 0.05 | 40 | ⊙ |
| 48 | 90 | 10 | 0.05 | 0.1 | 40 | ⊙ |
| 49 | 90 | 10 | 0.05 | 0.5 | 40 | ⊙ |
| 50 | 90 | 10 | 0.05 | 1.0 | 40 | ⊙ |
| 51 | 90 | 10 | 0.05 | 5 | 40 | ⊙ |

TABLE 8-continued

|    | Base Material F (wt %) | Antibacterial Material (wt %) | Amount of Metal (wt %) | Particle Diameter of Aggregate (m) | Porosity (%) | *1 Antibacterial Property |
|----|------------------------|-------------------------------|------------------------|------------------------------------|--------------|---------------------------|
| 52 | 90                     | 10                            | 0.05                   | 10                                 | 40           | ⊙                         |
| 53 | 90                     | 10                            | 0.05                   | 20                                 | 40           | O                         |
| 54 | 90                     | 10                            | 0.05                   | 40                                 | 40           | Δ                         |

*1 ... ⊙; Highly effective O; Effective Δ; A little effective X; Not effective

TABLE 9

| Example | Base Material F (wt %) | Antibacterial Material (wt %) | Amount of Metal (wt %) | Particle Diameter of Aggregate (m) | Porosity (%) | *1 Antibacterial Property |
|---------|------------------------|-------------------------------|------------------------|------------------------------------|--------------|---------------------------|
| 55      | 99                     | 1                             | 0.2                    | 0.5                                | 30           | ⊙                         |
| 56      | 97                     | 3                             | 0.6                    | 2                                  | 40           | ⊙                         |
| 57      | 90                     | 10                            | 2                      | 2                                  | 40           | ⊙                         |
|         | Base Material H (wt %) |                               |                        |                                    |              |                           |
| 58      | 99                     | 1                             | 0.2                    | 0.5                                | 30           | ⊙                         |
| 59      | 97                     | 3                             | 0.6                    | 2                                  | 40           | ⊙                         |
| 60      | 90                     | 10                            | 2                      | 2                                  | 40           | ⊙                         |

*1 ... ⊙; Highly effective O; Effective Δ; A little effective X; Not effective

As described above, according to the present invention, there are provided a lightweight antibacterial ceramic suitably applicable to a roof garden or the like, a method for producing the lightweight antibacterial ceramic, and an antibacterial ceramic filter capable of removing and extirpating various bacteria and suspensions because the bulk density and porosity of the sintered ceramic are controlled by mixing an antibacterial metal with particular materials and firing.

What is claimed is:

1. A lightweight antibacterial ceramic comprising:
   an antibacterial material of 0.01–20 wt % in which an antibacterial metal or metallic ion is loaded on a carrier; and
   an inorganic material of 99.9–80 wt %, said inorganic material being selected from the group consisting of an oxide inorganic material, a non-oxide inorganic material, and mixtures thereof;
   wherein said antibacterial ceramic has a particle bulk density of 0.6–2.0 g/cm$^3$.

2. A lightweight antibacterial ceramic according to claim 1, wherein said antibacterial material comprises an antibacterial metal or metallic ion of 0.01–20 wt % and a carrier of 99.9–80 wt %.

3. A lightweight antibacterial ceramic according to claim 1, wherein said antibacterial metal or metallic ion comprises at least one component selected from the group consisting of silver, copper, zinc, platinum, tin, arsenic, lead, cadmium, and chromium.

4. A lightweight antibacterial ceramic according to claim 1, wherein said carrier comprises at least one component selected from the group consisting of phosphate, silica, and zeolite.

5. A lightweight antibacterial ceramic according to claim 4, wherein said phosphate comprises at least one component selected from the group consisting of calcium phosphate, zinc phosphate, zirconium phosphate, and aluminum phosphate.

6. A lightweight antibacterial ceramic according to claim 5, wherein said calcium phosphate comprises at least one component selected from the group consisting of tricalcium phosphate, calcium hydrogenphosphate, calcium pyrophosphate, calcium metaphosphate, hydroxy apatite, and apatite halide.

7. A lightweight antibacterial ceramic according to claim 1, wherein said inorganic material is insoluble in water and substantially harmless to humans, animals, and plants.

8. A method for producing a lightweight antibacterial ceramic comprising the steps of:
   preparing an antibacterial ceramic material by loading an antibacterial metal or metallic ion on a carrier;
   mixing the obtained antibacterial ceramic material of 0.01–20 wt % with an inorganic material selected from the group consisting of an oxide inorganic material, a non-oxide inorganic material, and mixtures thereof of 99.9–80 wt % to obtain a first mixture;
   mixing a combustible material of 5–50 weight parts with 100 weight parts of the first mixture to obtain a second mixture; and
   firing the second mixture at a temperature of 500°–1300° C.

9. A method for producing a lightweight antibacterial ceramic according to claim 8, wherein said combustible material is selected from the group consisting of a carbon powder, a grain powder, and sawdust.

10. A method for producing a lightweight antibacterial ceramic according to claim 9, wherein the grain powder is wheat flour or rice flour.

11. An antibacterial ceramic filter comprising:

a base material phase of 99.9–80 wt % comprising an aggregate phase and an inorganic binder phase, said aggregate phase comprising a material selected from the group consisting of an oxide inorganic material, a non-oxide inorganic material, and mixtures thereof; and an antibacterial material of 0.01–20 wt % comprising a carrier and an antibacterial metal or metallic ion loaded on said carrier, wherein said antibacterial ceramic filter has a porosity of 20% or more.

12. An antibacterial ceramic filter according to claim 11, wherein said filter has a pore diameter ranging from 20 μm to 8000 μm.

* * * * *